United States Patent [19]
Suorsa et al.

[11] Patent Number: 5,474,074
[45] Date of Patent: Dec. 12, 1995

[54] LOW PROFILE TRANSDUCER FOR INTRAVASCULAR ULTRASOUND IMAGING AND METHOD FOR MOUNTING

[75] Inventors: Veijo Suorsa, Fremont; Peter Thornton, Costa Mesa; Mark Lentz, Sunnyvale, all of Calif.

[73] Assignee: Cardiovascular Imaging Systems, Incorporated, Sunnyvale, Calif.

[21] Appl. No.: 207,866

[22] Filed: Mar. 8, 1994

[51] Int. Cl.$^6$ .................................................... A61B 8/00
[52] U.S. Cl. .................................... 128/662.03; 29/25.35
[58] Field of Search ...................... 128/660.01, 660.07, 128/660.1, 662.03, 662.06, 663.01

[56] References Cited

U.S. PATENT DOCUMENTS

| | | | |
|---|---|---|---|
| 4,387,720 | 6/1983 | Miller | 128/663.01 |
| 4,841,977 | 6/1989 | Griffith et al. | 128/660.03 |
| 4,911,170 | 3/1990 | Thomas, III et al. | 128/662.06 |
| 4,917,097 | 4/1990 | Proudion et al. | 128/662.06 |
| 5,203,338 | 4/1993 | Jang | 128/662.06 |

OTHER PUBLICATIONS

"Approximate Material Properties in Isotropic Materials," Alan R. Selfridge, *IEEE Transactions on Sonics and Ultrasonics*, vol. SU–32, No. 3, pp. 381–394, May 1985.

*Primary Examiner*—Francis Jaworski
*Attorney, Agent, or Firm*—Townsend and Townsend and Crew

[57] ABSTRACT

An ultrasonic transducer includes a transducer element having a backing element bonded thereto. The thickness of the backing element is selected to be less than or equal to half the length of an ultrasonic pulse, expressed in wavelengths of the center frequency of the pulse, so that the first reflection from the back side of the backing element is received by the transducer element before the primary pulse rings down. A method for mounting the transducer that reduces the formation of air bubbles includes the steps of forming a peaked mound and continually lowering the transducer to flatten the mound against the underside of the transducer.

4 Claims, 3 Drawing Sheets

LOW PROFILE TRANSDUCER FOR INTRAVASCULAR ULTRASOUND IMAGING AND METHOD FOR MOUNTING

BACKGROUND OF THE INVENTION

1. Field of the Invention

The present invention relates generally to ultrasonic transducer design and more particular to the design of ultrasonic transducers for use in vascular catheters to form images of stentonic regions within a blood vessel.

2. Description of the Relevant Art

Intravascular imaging catheters which include ultrasonic transducers are well-known. Most often, imaging catheters capable of providing real time images through 360° have an ultrasonic transducer that is axially mounted, i.e., mounted so that an ultrasonic pulse is transmitted principally along the catheter axis, and use an acoustic mirror to reflect the ultrasonic pulse in a direction perpendicular to the catheter axis. Alternatively, a side looking transducer, i.e., a transducer mounted so that an ultrasonic pulse is transmitted in a direction perpendicular to the catheter axis, may be utilized without a mirror. Examples of several transducer configurations are disclosed in the commonly assigned U.S. Pat. No. 5,000,185 to Yock.

When the ultrasonic transducer is excited it "rings" at a resonant frequency for a small period of time before the ringing is mechanically damped to an insignificant magnitude. Thus, an ultrasonic pulse having a characteristic duration defined in microseconds and length defined in microns is emitted by the transducer. Typically, a transducer includes a transducer element having first and second oppositely disposed major surfaces with a backing element bonded to the second major surface. Most of the ultrasonic energy generated by the transducer element is emitted as pulses propagating in directions perpendicular to the major surfaces. The backing element attenuates reflections of an ultrasonic pulse emitted into the backing element to prevent multiple pulses from being emitted in the direction perpendicular to the first major surface. The primary mechanisms of attenuation are propagation loss, with the amount of attenuation dependent on the distance travelled by the pulse, and reflection loss, with the amount of attenuation determined by mismatch of the impedances at the boundaries of the backing element. This backing element also affects the mechanical damping of the transducer and forms part of the mounting structure of the transducer to the catheter.

To form high-quality intravascular images it is required that only a single ultrasonic pulse is transmitted when the transducer element is excited by an electric pulse and that a single electric pulse be emitted when the transducer element is excited by an ultrasonic pulse. Thus, to prevent the generation of multiple pulses the backing element is fabricated of a sound attenuating material and is thick enough so that reverberations reflecting off the interface of the backing element and a back filling material are attenuated by propagation loss to acceptable levels.

It is generally desirable to minimize the diameter of the catheter to permit its insertion into small diameter blood vessels. The thickness of the backing is usually not critical for an axially mounted transducer because the thickness of the backing does not affect the diameter of the catheter. However, for a side looking transducer often the minimum diameter of the catheter is determined by the thickness of the transducer and backing.

In some applications it is desirable to use a side looking transducer because the mirror strut in the axial system can cause artifacts and the acoustic coupling between the flushing liquid in the catheter and the transducer is improved. However, the use of a side looking transducer having a backing element thick enough to attenuate reverberations to prevent the generation of multiple pulses places a lower limit on the diameter of the catheter which may limit its utility.

SUMMARY OF THE INVENTION

The present invention is an improved ultrasonic transducer having a thin profile that prevents reverberations in the backing from generating multiple pulses.

According to one aspect of the invention, a transducer is designed which generates an electric pulse having a temporal duration of t microseconds when excited by a received ultrasonic pulse and transmits an ultrasonic pulse which has a temporal duration of t microseconds and spatial length of L microns when the transducer element is excited by an electric pulse. The length L is also equal to a number, NW, of wavelengths of a center frequency of the derivative ultrasonic pulse. A backing element is bonded to a transducer element and has a thickness of less than or equal to about NW/2 wavelengths at the center frequency.

According to another aspect of the invention, the transducer is mounted in a housing utilizing a bed fabricated of a filler material.

According to another aspect of the invention, the mounting of the transducer on the bed includes the steps of forming a peaked mound of filling material, positioning the transducer so that the point of the peak is located at approximately the center of a major surface of the transducer, and continuously lowering the transducer to flatten the peaked mound against the major surface of the transducer to form a bond that is substantially free of air bubbles.

Other advantages and features of the invention will be apparent in view of the following detailed description and appended drawings.

DESCRIPTION OF THE PREFERRED EMBODIMENT

Figure 1A:
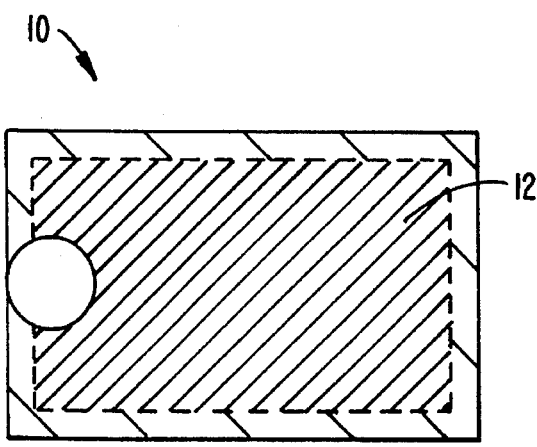
FIGS. 1A and 1B are schematic diagrams of a transducer.
Figure 1B:
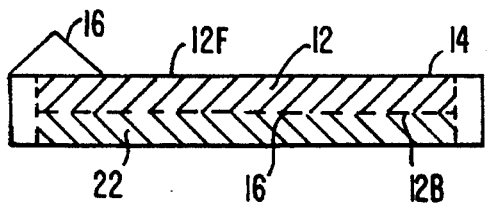
Figure 2:
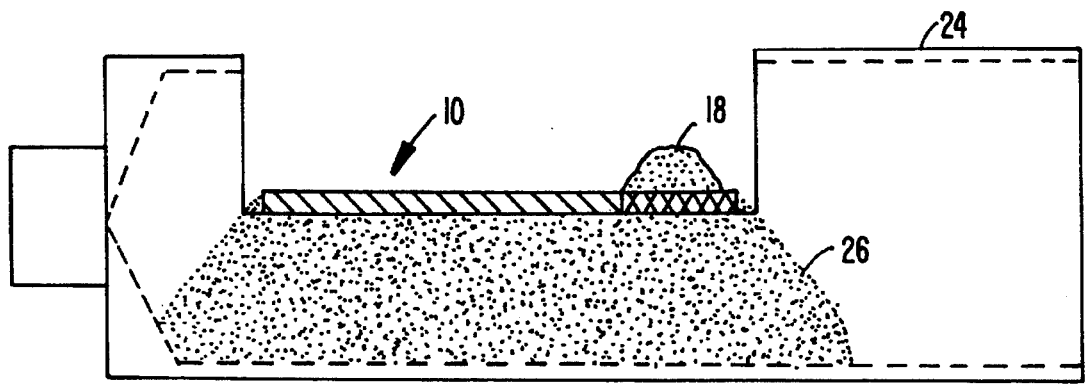
FIG. 2 is a schematic diagram of a transducer mounted in a housing.
Figure 3:
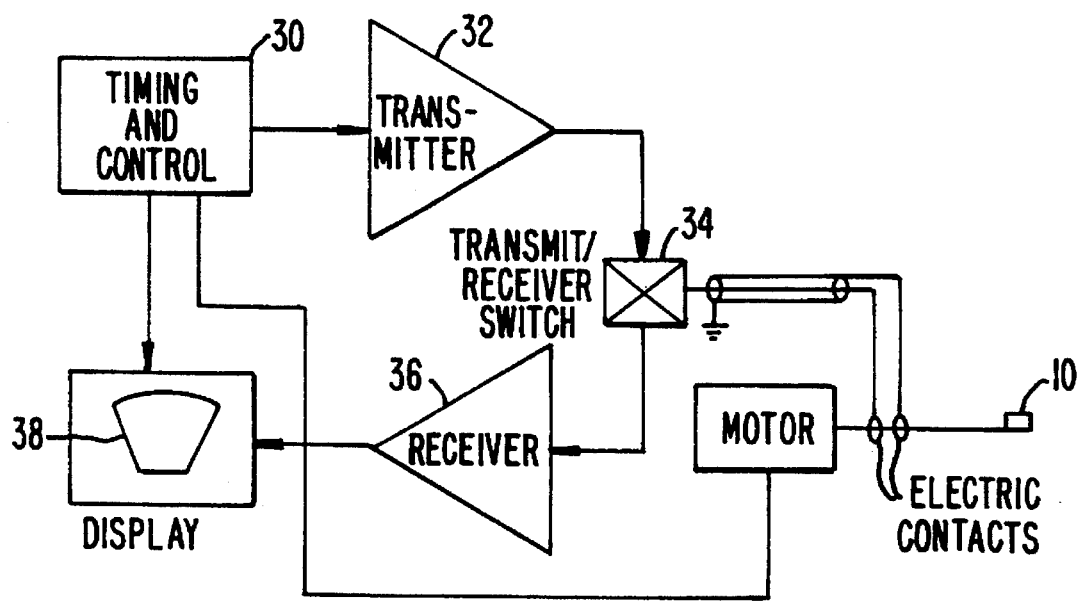
FIG. 3 is a block diagram of a control system.

FIGS. 1A and 1B are schematic diagrams depicting an ultrasonic transducer system for emitting and detecting pulses of ultrasonic energy; FIG. 2 is a schematic diagram of the transducer mounted in a distal housing of a catheter; and FIG. 3 is a schematic diagram of a typical system for exciting the transducer to emit an ultrasonic pulse and to detect a received ultrasonic pulse.

Turning first to FIGS. 1A and 1B, the ultrasonic transducer 10 includes a single transducer element 12 which is part of an assembly. The function of the transducer element 12 is to convert ultrasonic pulses to electric pulses and electric pulses to ultrasonic pulses and the transducer element is fabricated from PZT ceramic material. The transducer element 12 has a block-like configuration and includes front and back opposing surfaces 12F and 12B covered by metallic conducting films 14 and 16 formed of a suitable material such as chrome or gold. The material of the films can be formed of a foil or can be in the form of films evaporated or sputtered onto the opposing surfaces of the transducer element 12. The films 14 and 16 serve as electrodes and the front electrode 14 has a silver epoxy dot 18 disposed thereon to be connected to a wire. The transducer element 12 may have a ¼-wave impedance matching layer on the front surface which is not shown in the figure.

A backing element 22 of a suitable backing material is bonded to the back surface of the transducer element 12 to attenuate ultrasonic energy emitted by the back face 12B of the transducer element 12. The backing element 22 has a front surface 22F bonded to the back surface 12B of the transducer element 12. The particular structure of the backing element 22 will be described below.

FIG. 2 depicts a transducer 10 mounted in a distal housing 24. The transducer 12 is mounted on a bed 26 of filler material, such as silver epoxy, and the back surface 22B of the backing element 22 is in contact with the bed 26. In the preferred embodiment, the backing element 22 and the bed 26 are fabricated of electrically conductive materials and function as a conductive path forming the electrical contact to the back electrode 16.

Turning now to FIG. 3, a typical system for energizing the transducer 10 to emit ultrasonic pulses and for detecting received pulses is depicted. This system is not part of the invention and will be described only briefly. A timing and control block 30 controls a transmitter 32 to emit a series of voltage pulses of a predetermined duration separated by a predetermined intervals. The switch 34 couples the transmitter 32 to the transducer 10 when the pulses are generated and couples a receiver 36 to the transducer 10 during the intervals between pulses.

The received pulses are processed by an image generating system 38 which is not part of the invention. The primary information utilized to generate an image is the delay time between the transmission of an ultrasonic pulse and the receipt of the received pulse. Other information such as the amplitude and phase of the received pulse can also be processed.

As is well-known, when a voltage pulse is applied to the electrodes 14 and 16 the transducer element 12 oscillates to generate a pulse centered on a resonant frequency determined by the mechanical and piezoelectric properties of the transducer 10. Thus, a series of ultrasonic pulses separated by the predetermined interval is transmitted.

Conversely, when an ultrasonic pulse is received by the transducer 10 a voltage pulse is generated on the electrodes 14 and 16 which is amplified by the receiver 36 and transmitted to the image generating system 38.

Figure 4:
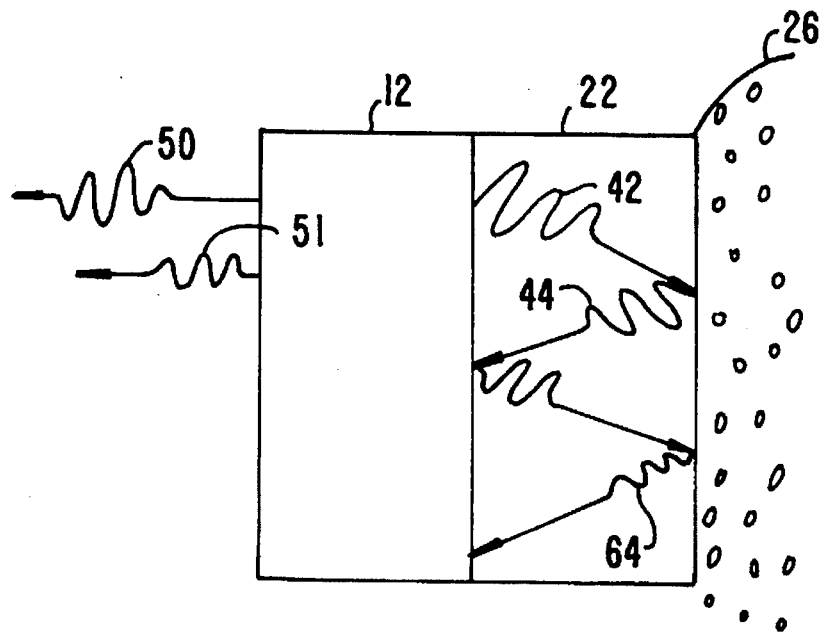
FIG. 4 a diagram depicting derivative and reflected ultrasonic pulses in a backing element.
Figure 5:
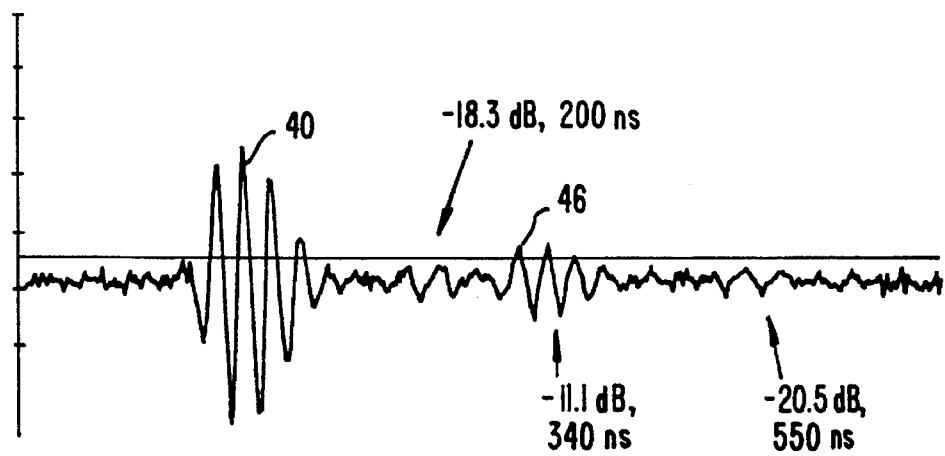
FIG. 5 is a graph depicting primary and secondary electric pulses in a system utilizing a thick backing element.

FIGS. 4 and 5 depict the response of the transducer 10 when a reflected ultrasonic pulse is received to generate an electric pulse and when an electric pulse is received to transmit an ultrasonic pulse. FIG. 4 is a simplified block diagram of the transducer element 12, backing 22, and bed 26 and FIG. 5 is a graph of the voltage response of the transducer element 12 when an ultrasonic pulse is received.

The operation of transducer 10 to detect a received ultrasonic pulse will now be described. When an ultrasonic pulse impinges on the transducer 10 the transducer element 12 generates a primary voltage pulse 40 across the electrodes 14 and 16. When the same transducer is used on transmit and receive, the bandwidth of the ultrasonic pulse received by the transducer 10 is centered on a center frequency, $f_r$, approximately equal to the resonant frequency of the transducer element 12 and results in a derivative ultrasonic pulse 42 which propagates through the backing element 22. The derivative ultrasonic pulse 42 is reflected at the interface of the back surface 22B of the backing element 22 and the filler material 26 to form a first reflected ultrasonic pulse 44 which impinges on the transducer element 12 after a time determined by the thickness of the backing and the acoustic velocity of the pulse in the backing material.

Mathematically, if "c" is the acoustic velocity of the pulse in the backing element, "LB" is the thickness of the backing element, and "t" is the transit time, then:

$$t = 2LB/c \qquad \text{Equation (1)}$$

As depicted in FIG. 5, a secondary electric pulse 46 is generated when the first reflected ultrasonic pulse 44 impinges on the transducer element 12. The primary electric pulse 40 generated when the ultrasonic pulse reflecting from the vascular walls impinges on the transducer element 12 provides information required to form an image of a blood vessel. On the other hand, the secondary electric pulse 46 is caused by a reverberation from the backing element 22 and conveys no information. However, this secondary electric pulse 46 may be processed by the image generating system 38 to form an "artifact" in the image conveying false information or masking true information.

Next, the operation of the transducer 10 to transmit an ultrasonic pulse when excited by an electric pulse provided by the transmitter 32 will be described. Referring again to FIG. 4, when a voltage pulse is provided to the electrodes 14 and 16 the transducer element 12 rings to produce a primary ultrasonic pulse 50 which propagates outward from the front surface 12F into the vascular medium and a derivative ultrasonic pulse 42 which propagates outward from the back face 12B into the backing element 22. A portion of the derivative ultrasonic pulse 42 is reflected from the interface between the backing element 22 and the back fill material 26 to form a reflected pulse which propagates through the transducer element 12 into the vascular medium to form a secondary ultrasonic pulse 51. Thus, multiple ultrasonic pulses will be generated unless the reflected pulses are attenuated. If multiple ultrasonic pulses are transmitted then the primary and secondary ultrasonic pulses 50 and 51 will be reflected by the vascular walls and be detected by the transducer 12. The detected secondary ultrasonic pulse 51 will cause an artifact in the image.

Conventionally, referring to FIG. 4, the amplitude of the reflected ultrasonic pulse 44 is attenuated by propagation loss as it propagates through the backing element. However, for a side looking transducer the thickness to the backing material is limited and acceptable attenuation due to propagation loss is not possible resulting in the generation of multiple pulses.

In FIG. 5, the transducer element 12 is designed to resonant at a center frequency of 30 MHz and generate a pulse having a length in number of wavelengths, NW, of about 4.5. The spatial length, L, is related to the temporal duration dt, by the mathematical relationship:

$$dt = L/c \quad \text{Equation (2)}$$

and the wavelength, "w" is related to frequency, "f" by the relationship:

$$w = c/f \quad \text{Equation (3)}$$

As is well-known, the velocity of the ultrasonic pulse in a medium is dependent on the density and elastic properties of the medium. The values of the velocity and density for different materials are available in the scientific literature, for example in the paper entitled "Approximate Material Properties in Isotropic Materials," by Alan R. Selfridge, published in *IEEE Transactions On Sonics and Ultrasonics*, Vol. SU-32, No. 3, May 1985.

Using equation 3, the wavelength for a resonant frequency of 30 MHz is approximately 63 microns and the temporal duration of the primary pulse is about 150 nanoseconds.

Figure 6:
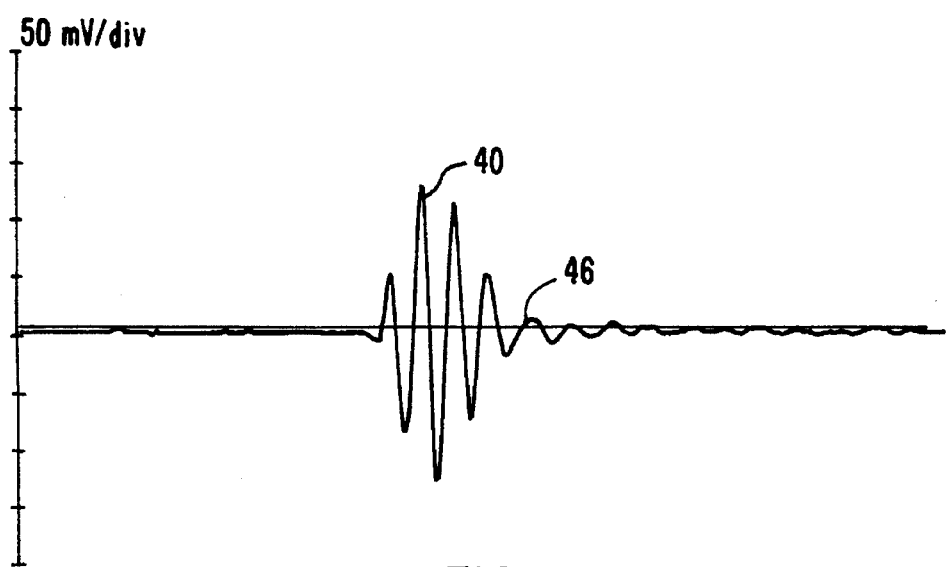
FIG. 6 is a graph depicting the primary and secondary electric pulses for a preferred embodiment of the invention.

The principle of operation of the present invention is illustrated in FIGS. 4–6. The thickness of the backing element 22 is selected so that the first reflected ultrasonic pulse 44 arrives at the transducer element 12 during the ringdown period of transducer 10 and higher order reflected ultrasonic pulses are attenuated due to propagation loss and by reflection loss due to multiple reflections from the front and back surfaces 22F and 22B of the backing element 22.

As depicted in FIG. 6, the secondary electric pulse 46, resulting from the first reflected ultrasonic pulse impinging on the transducer 10, overlaps the ring down of the primary electric pulse 40. Since the most important information conveyed is the time of receipt of the primary electric pulse 40, the addition of the secondary electric pulse 46 to the tail of the primary electric pulse 40 will not degrade this information or cause artifacts.

Thus, when detecting a received ultrasonic pulse, the combined times of transit of the derivative ultrasonic pulse 42 and the reflected ultrasonic pulses 44 through the backing must be less that the temporal duration, e.g. 150 nanoseconds, of the primary electric pulse 40. If LB is the thickness of the backing element 22, then the derivative ultrasonic pulse 42 travels a distance of LB and the first reflected ultrasonic pulse 44 travels a distance of LB so that the total combined transit distance travelled by the ultrasonic pulse in the backing is twice the thickness of the backing element 22, i.e., 2LB, before the reflected ultrasonic pulse 44 impinges on the transducer element 12. Utilizing Equation (2) to relate distance and time, the thickness of the backing element 22 must be less than or equal to:

$$LB = (dt \times c)/2 \quad \text{Equation (4)}$$

Alternatively, LB can be expressed in terms of wavelengths for ultrasonic radiation in the backing at the center frequency. If NW is the length of the primary pulse in terms of wavelengths at the center frequency, $f_r$, then the width of the backing must be less than or equal to:

$$LB(\text{in wavelengths}) = NW/2 \quad \text{Equation (5)}$$

The formulation of equation (5) permits calculation of the thickness of the backing element for selected resonant frequency if the value of c for the backing element material is known.

As stated above, because the backing element 22 is very thin, the attenuation due to reflection loss is significant. As the ultrasound pulse bounces back and forth between the front and back faces of the backing element 22 only a portion of the ultrasonic pulse is reflected back from the boundary because of acoustic impedance mismatch at the faces. The normal incidence reflection coefficient, $R_B$, at the back face of the backing is expressed mathematically as:

$$R_B = (Z_F - Z_B)/(Z_F + Z_B) \quad \text{Equation (6)}$$

where $Z_B$ is the acoustic impedance of the backing material and $Z_F$ is the acoustic impedance of the filling material on the rear side of the backing. For instance, if $Z_B$ is 3 and $Z_F$ is 1.5 MRayl, then $R_B$ is −0.3333, i.e. about 33% of the of the ultrasonic wave is reflected with its phase reversed as indicated by the minus sign of the reflection coefficient. In a similar way, the reflection coefficient, $R_F$, at the front surface of the backing is expressed mathematically as:

$$R_F = (Z_T - Z_B)/(Z_T + Z_B) \quad \text{Equation (7)}$$

where $Z_T$ is the acoustic impedance of the transducer element 12. Typically, $Z_T$ is about 33 and if $Z_B$ is 3 MRayl, then $R_F$ is about 0.8333, i.e. about 83% of the of the reflected secondary pulse is reflected into the backing again.

As depicted in FIG. 4, the amplitude of the second reflection 64 is highly attenuated due to two extra reflections after the ultrasound has travelled four times the backing thickness LB, i.e., 4 LB compared to a single reflection after propagating through a backing of thickness 2 LB, but the same propagation length 4 LB. Mathematically, the amplitude loss due to two extra reflections is expressed by the product of equations (6) and (7):

$$R_B \times R_F = (Z_F - Z_B)/(Z_F + Z_B) \times (Z_T - Z_B)/(Z_T + Z_B) \quad \text{Equation (8)}$$

i.e., if $Z_B=3$, $Z_F=1.5$, and $Z_T=33$ MRayl, the amplitude of the second reflection 64 is reduced to only 28% of that of a propagation path with a single reflection but of equal distance.

Thus, the selected thickness of the backing element 22 results in the first reflection being absorbed into the primary pulse and the second reflection being highly attenuated due to reflection loss caused by extra reflections at the backing boundaries.

Referring back to FIG. 2, the bond between the back surface of the backing element 22 of transducer 10 and bed 26 should be free of air bubbles to assure good acoustic coupling. A method for forming such a bond will now be described with reference to FIGS. 2 and 7.

Figure 7:
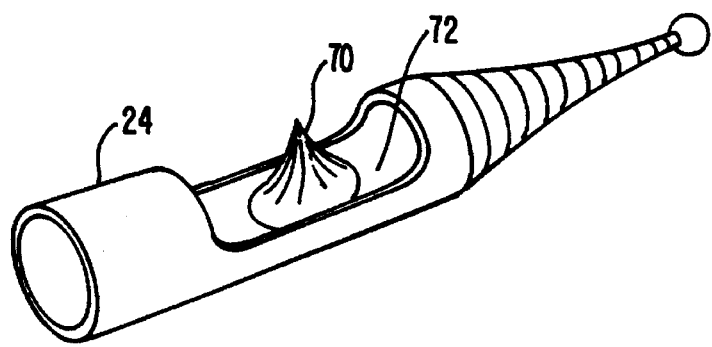
FIG. 7 is a diagram depicting a peaked mound of filler material in the trough of a housing.

In FIG. 7, a peaked mound 70 of conductive filler material, such as silver epoxy, is formed in a trough 72 of the housing 24. The transducer 10 is then positioned so that pointed top of the peaked mound touches the back surface of the transducer 10 near the center of the back surface. The transducer 10 is then continuously lowered to flatten the pointed top of the peaked mound against the back surface of the transducer 10. It has been discovered that by utilizing a peaked mound and continuously lowering the transducer 10 with no reversing of motion substantially no air is trapped between the back face of the transducer 10 and the bed 26.

The invention has now been described with reference to the preferred embodiments. Alternatives and substitutions will now be apparent to persons of skill in the art. For example, although the transducer element 12 utilized in the preferred embodiment is a PZT ceramic element, other transducer elements such as, for example, piezoelectric polymers like PVDF or piezoelectric composite materials can be utilized. Additionally, the principle of the invention can be applied to a transducer array consisting of multiple transducer elements. Further, the principles of the invention can be applied to transducer elements, such as focused or tapered transducer elements, having non-planar major surfaces. Accordingly, the invention is not intended to be limited except as provided by the appended claims.

What is claimed is:

1. A system for transmitting and receiving ultrasonic pulses comprising:

an ultrasonic transducer element having first and second transducer element major surfaces and dimensions selected so that said transducer element oscillates at a selected resonant center frequency $f_r$;

means, mechanically coupled to said transducer element, for generating an electric pulse, having a temporal duration of about t microseconds, when said transducer element is excited by a received ultrasonic pulse and for providing an electric excitation pulse causing said transducer element to transmit a primary ultrasonic pulse having a spatial length of L microns, and a temporal duration of t microseconds, where L is approximately equal to a predetermined multiple of the wavelength the resonant center frequency, $f_r$, of the ultrasonic waves forming said primary ultrasonic pulse; and a backing element, having first and second backing element major surfaces and formed of a high-loss material for attenuating an ultrasonic pulse traversing the backing material, with the first backing element major surface bonded to the second transducer element major surface of said transducer element and with the distance between the first and second major surfaces of said backing element being equal to about one half said predetermined number of wavelengths at the center frequency, $f_r$, so that an ultrasonic pulse reflected from the second backing element major surface is received at the second major surface of the transducer element within t microseconds of the excitation of said transducer element and so that ultrasonic pulses reflected a plurality of times from the second backing element major surfaces are highly attenuated due to propagation and reflection loss.

2. The system of claim 1 further comprising:

a housing;

a bed of filler material having said second backing element surface bonded thereto and mechanically coupling said second backing element to said housing.

3. A method of mounting a structurally rigid. sideways-looking ultrasonic transducer in an intravascular catheter, the transducer having first and second substantially planar major surfaces, said method comprising the steps of:

providing a housing, forming part of the intravascular catheter and having a diameter suitable for insertion into small blood vessels, characterized by a catheter axis defining the direction of insertion, and with the housing having a trough including a bottom supporting surface oriented parallel to the housing diameter;

providing a predetermined amount of a filler material;

forming said filler material into a peaked mound, having a substantially pointed top and a base, with the base disposed on the bottom supporting surface of said trough;

positioning said transducer so that the pointed top of said peaked mound touches the second major surface at a point near the center of said second major surface; and continuously lowering said positioned transducer element to flatten the peaked mound against the second major surface of said transducer to form a bond between said transducer and said filler material that is substantially free of air bubbles.

4. A method of mounting a structurally rigid, sideways looking ultrasonic transducer in an intravascular catheter, the transducer having first and second substantially planar major surfaces, said method comprising the steps of:

providing a housing, forming part of the intravascular catheter and having a diameter suitable for insertion into small blood vessels, characterized by a catheter axis defining the direction of insertion, and with the housing having a trough including a bottom supporting surface oriented parallel to the housing diameter;

providing a predetermined amount of silver epoxy;

forming said silver epoxy into a peaked mound, having a substantially pointed top and a base, with the base disposed on the bottom supporting surface of said trough;

positioning said transducer so that the pointed top of said peaked mound touches the second major surface at a point near the center of said second major surface; and continuously lowering said positioned transducer element to flatten the peaked mound against the second major surface of said transducer to form a bond between said transducer and said silver epoxy that is substantially free of air bubbles.

* * * * *